(12) United States Patent
Kizuka

(10) Patent No.: US 10,149,685 B2
(45) Date of Patent: Dec. 11, 2018

(54) SYSTEM AND METHOD FOR MITRAL VALVE FUNCTION

(71) Applicant: Abbott Cardiovascular Systems Inc., Santa Clara, CA (US)

(72) Inventor: Koji J. Kizuka, San Francisco, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 130 days.

(21) Appl. No.: 15/445,789

(22) Filed: Feb. 28, 2017

(65) Prior Publication Data
US 2018/0242976 A1   Aug. 30, 2018

(51) Int. Cl.
| | |
|---|---|
| A61F 2/24 | (2006.01) |
| A61B 17/122 | (2006.01) |
| A61B 17/128 | (2006.01) |
| A61B 17/00 | (2006.01) |

(52) U.S. Cl.
CPC ........ *A61B 17/122* (2013.01); *A61B 17/1285* (2013.01); *A61F 2/2463* (2013.01); *A61F 2/2466* (2013.01); *A61B 2017/00867* (2013.01); *A61F 2210/0014* (2013.01)

(58) Field of Classification Search
CPC .......... A61B 17/122; A61B 2017/1225; A61B 17/1227; A61B 17/128; A61B 17/1285; Y10T 24/3424; Y10T 24/45775; Y10T 24/45785; Y10T 24/45791; A44B 17/00; A44B 17/0005; A44B 17/0023; A44B 17/0041
See application file for complete search history.

(56) References Cited

U.S. PATENT DOCUMENTS

| | | | | |
|---|---|---|---|---|
| 1,241,922 | A * | 10/1917 | Chappell | F41A 9/84 224/247 |
| 2,797,886 | A * | 7/1957 | Pinckney | A47K 1/09 15/246 |
| 3,807,675 | A * | 4/1974 | Seckerson | F16L 3/13 24/337 |
| 3,944,177 | A * | 3/1976 | Yoda | F16L 3/08 248/74.2 |
| 4,470,179 | A * | 9/1984 | Gollin | F16L 3/13 24/297 |
| 4,931,058 | A * | 6/1990 | Cooper | A61B 17/1227 24/523 |
| 4,977,648 | A * | 12/1990 | Eckerud | E05C 19/066 24/324 |

(Continued)

*Primary Examiner* — Wade Miles
(74) *Attorney, Agent, or Firm* — David J. Pitman; Fulwider Patton LLP

(57) ABSTRACT

A system for repairing a mitral valve: a first cylinder; and, a clip having an axial length and comprising a second cylinder having a wall and an internal bore. The wall defines an opening extending along the axial length, the opening being sized for at least two requirements: (a) the opening is large enough to receive the first cylinder when the first cylinder is positioned parallel with and adjacent to the second cylinder and the first cylinder is moved in a direction, through the opening. The wall of the second cylinder is sized to bend elastically to widen the opening so as to receive the first cylinder; and (b) the opening is small enough to prevent the first cylinder from falling out of the bore.

9 Claims, 8 Drawing Sheets

(56) References Cited

U.S. PATENT DOCUMENTS

| | | | |
|---|---|---|---|
| 5,896,720 A * | 4/1999 | Bond | E04D 13/12 24/336 |
| 8,052,592 B2 | 11/2011 | Goldfarb et al. | |
| 8,099,837 B2 * | 1/2012 | Santin | A47C 31/023 24/297 |
| 2003/0215601 A1 * | 11/2003 | Pedde | B29C 33/12 428/102 |
| 2006/0264987 A1 * | 11/2006 | Sgro | A61B 17/12013 606/157 |
| 2012/0116369 A1 * | 5/2012 | Viola | A61B 17/00234 606/1 |
| 2016/0038149 A1 | 2/2016 | Ladjali | |

* cited by examiner

SYSTEM AND METHOD FOR MITRAL VALVE FUNCTION

BACKGROUND

The present invention relates generally to medical methods, devices, and systems. In particular, the present invention relates to methods, devices, and systems for the endovascular, percutaneous or minimally invasive surgical treatment of bodily tissues, such as tissue approximation or valve repair. More particularly, the present invention relates to repair of valves of the heart and venous valves.

Surgical repair of bodily tissues often involves tissue approximation and fastening of such tissues in the approximated arrangement. When repairing valves, tissue approximation includes coapting the leaflets of the valves in a therapeutic arrangement which may then be maintained by fastening or fixing the leaflets. Such coaptation can be used to treat regurgitation which most commonly occurs in the mitral valve.

Mitral valve regurgitation is characterized by retrograde flow from the left ventricle of a heart through an incompetent mitral valve into the left atrium. During a normal cycle of heart contraction (systole), the mitral valve acts as a check valve to prevent flow of oxygenated blood back into the left atrium. In this way, the oxygenated blood is pumped into the aorta through the aortic valve. Regurgitation of the valve can significantly decrease the pumping efficiency of the heart, placing the patient at risk of severe, progressive heart failure.

Mitral valve regurgitation can result from a number of different medical defects in the mitral valve or the left ventricular wall. The valve leaflets, the valve chordae which connect the leaflets to the papillary muscles, the papillary muscles or the left ventricular wall may be damaged or otherwise dysfunctional. Commonly, the valve annulus may be damaged, dilated, or weakened limiting the ability of the mitral valve to close adequately against the high pressures of the left ventricle.

The most common treatments for mitral valve regurgitation rely on valve replacement or repair including leaflet and annulus remodeling, the latter generally referred to as valve annuloplasty. A recent technique for mitral valve repair which relies on suturing adjacent segments of the opposed valve leaflets together is referred to as the "bow-tie" or "edge-to-edge" technique. While all these techniques can be very effective, they usually rely on open heart surgery where the patient's chest is opened, typically via a sternotomy, and the patient placed on cardiopulmonary bypass. The need to both open the chest and place the patient on bypass is traumatic and has associated high mortality and morbidity.

Consequently, alternative and additional methods, devices, and systems for performing the repair of mitral and other cardiac valves have been developed. Such methods, devices, and systems preferably do not require open chest access and are capable of being performed either endovascularly, i.e., using devices which are advanced to the heart from a point in the patient's vasculature remote from the heart or by a minimally invasive approach.

In some instances, however, a variety of challenges are faced in desirably correcting the valve leaflets. For example, it is frequently found that one of the leaflets has become extended in length, and will not form a seal with the opposing leaflet under known methods of repair.

Therefore, devices, systems and methods are desired which may shorten and stabilize the tissue of the leaflet, to improve coaptation with an opposing leaflet. At least some of these objectives will be met by the embodiments described herein below.

SUMMARY OF THE INVENTION

In one embodiment, the invention is a system for repairing a mitral valve in a patient's heart. The system comprises a first cylinder; and a clip having an axial length and comprising a second cylinder having a wall and an internal bore, wherein the wall defines an opening extending along the axial length. The opening is sized to satisfy at least two requirements. First, the opening must be large enough to receive the first cylinder when the first cylinder is positioned parallel with and adjacent to the second cylinder and the first cylinder is moved in a direction, radially with respect to the second cylinder, through the opening into the bore at the same time that a portion of a leaflet in the mitral valve is positioned in the bore between the first cylinder and the second cylinder, wherein, the wall of the second cylinder is sized to bend elastically to widen the opening so as to receive the first cylinder. Second, the opening must be small enough to prevent the first cylinder from falling out of the bore, once the first cylinder has been received into the bore of the second cylinder.

In some embodiments, the clip includes two elongate flanges, each flange extending from the second cylinder. In further embodiments each of the two flanges are formed from a shape memory alloy and in yet other embodiments, each of the two flanges define a surface that is planar. Where two flanges are present each of the two flanges may be configured to be wrapped around the second cylinder when in a delivery condition, and extending perpendicular to the axial length in a deployment condition. The clip may be made of polymer, or it may be made of shape memory alloy.

In another embodiment, the invention is a method of repairing a mitral valve in a patient's heart. The method comprises positioning, above a leaflet of the mitral valve, a first cylinder. Then, below the leaflet, a clip is positioned. The clip has an axial length and comprising a second cylinder having a wall and an internal bore, wherein the wall defines an opening extending along the axial length. The first cylinder is pressed radially toward the second cylinder and through the opening into the bore, and simultaneously forcing a portion of the leaflet into the bore between the first cylinder and the second cylinder.

In some embodiments, pressing the first cylinder through the opening into the bore includes elastically bending the second cylinder to temporarily widen the opening. In other embodiments of the method, positioning a first cylinder and positioning a clip are performed using a transeptal procedure. And in other embodiments, the method further includes positioning an elongate element to extend along a free edge of the leaflet.

In yet another embodiment, the invention is a method for repairing a mitral valve in a patient's heart. The method comprises inserting into a left atrium of the patient's heart by transeptal procedure a pair of opposable cutting elements. Then, with the cutting elements, cutting through a posterior leaflet of the mitral valve thereby separating the posterior leaflet into a left portion bounded by a left cut edge, and a right portion bounded by a right cut edge. Thereafter, the method comprises pulling the left portion towards the right portion thereby shortening a free edge of the posterior leaflet. Once this has been achieved, the left portion is connected to the right portion. In some embodiments, joining the left portion to the right portion includes capturing the left cut edge and the right cut edge between a left set of opposing jaws and a right set of opposing jaws respectively. In other embodiments, pulling the left portion towards the right portion includes aligning the left set of opposing jaws to extend substantially parallel with the right set of opposing jaws.

DETAILED DESCRIPTION OF THE PREFERRED EMBODIMENTS

With reference to the figures, a description is provided of some embodiments having features of the invention. As used herein, the term "transcatheter" is used to describe a minimally invasive technique to enter the heart using a catheter via lumens that give access to the heart, and may include penetrating a wall such as a septum with the catheter.

Figure 1:
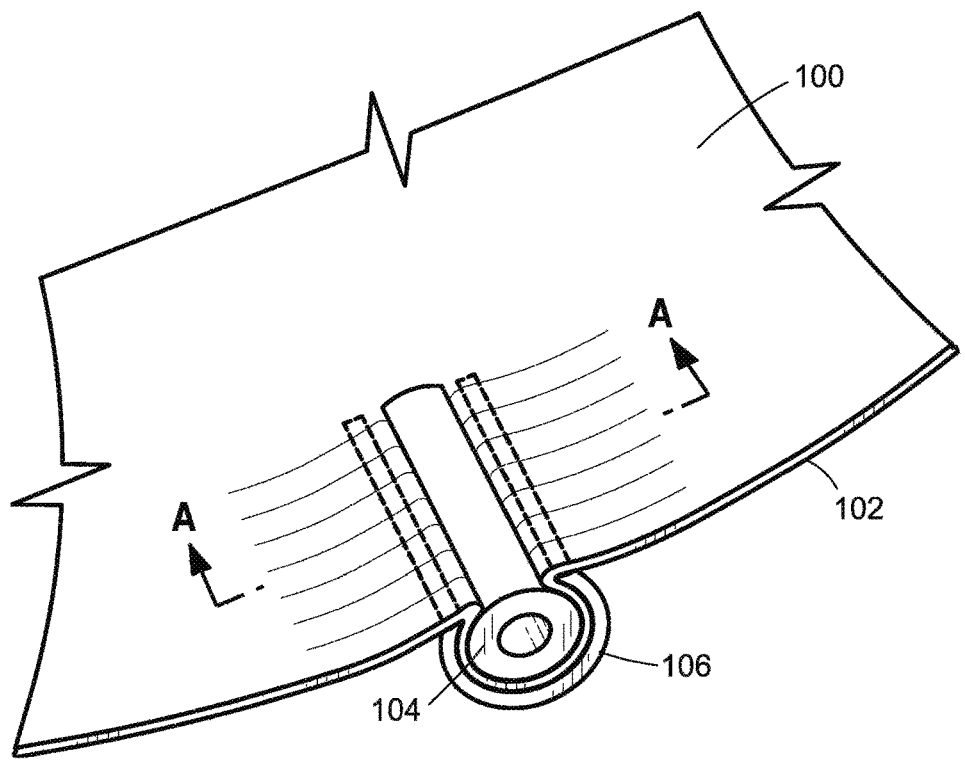
FIG. 1 is a perspective schematic view of one embodiment of the invention, shown attached to a leaflet of a mitral valve.
Figure 2:
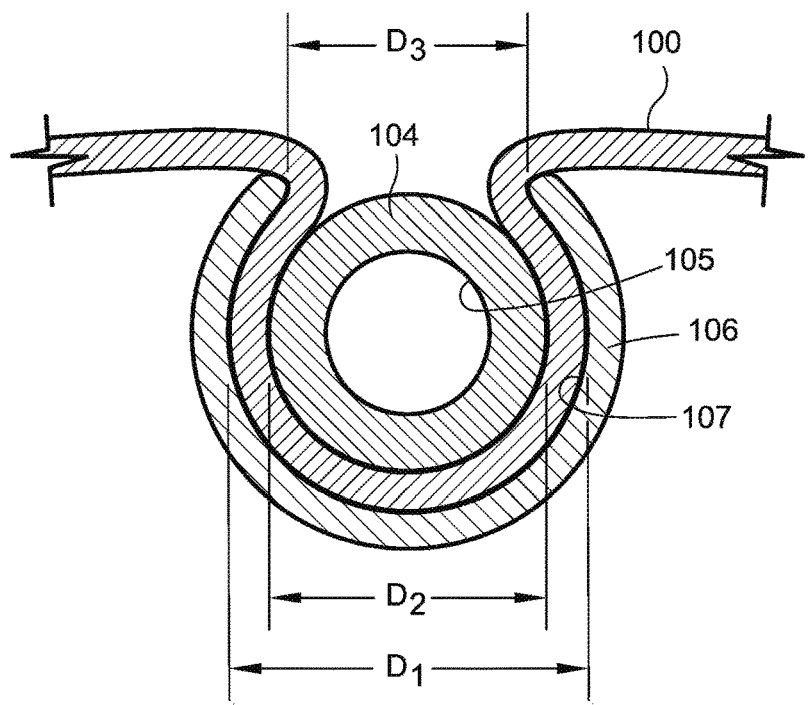
FIG. 2 is a sectional view taken substantially along the line A-A in FIG. 1.
Figure 4:
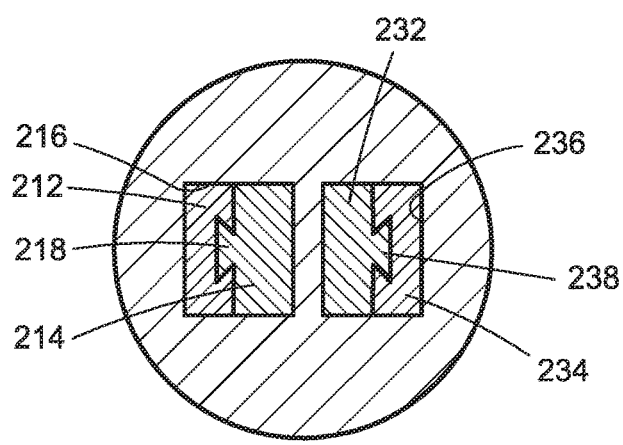
FIG. 4 is a sectional view, taken substantially along the line A-A in FIG. 3.

FIG. 1 and FIG. 2 show a single leaflet 100 of a bicuspid valve which has a free edge 102. Before the invention is applied to the leaflet, the free edge 102 of the leaflet may have become stretched or degraded, so that it no longer forms an effective coaptation, or seal, with an opposing leaflet. As a consequence, regurgitation of the valve tends to take place and the health of the patient is compromised. The purpose of the invention described herein is to shorten the effective length of the free edge 102, in order to improve coaptation of opposing leaflets, and reduce regurgitation. Preferably, as will be described further herein below, the leaflet to be operated upon will likely be the posterior leaflet, rather than the anterior leaflet, due to the fact that the posterior leaflet extends around the outside radius of a bend in the aperture of the mitral valve (FIG. 16) so that shortening of the free edge of this leaflet results in improved coaptation of the valve.

The novel solution described by the present invention involves, in some embodiments, attaching only two separate elements to the leaflet 100 with the effect of taking up slack in the leaflet. Thus, in some embodiments, the invention may consist of only a hollow cylinder 104 defining an internal bore 105, and a clip 106 comprising an internal bore 107. As understood with reference to FIG. 2, an end view of the invention in a condition where it is applied to the leaflet, the clip 106 has an internal bore 107 which is shown to have an internal diameter D1 that is larger than the external diameter D2 of the cylinder 104. D1 is sufficiently large to receive both the cylinder and also the leaflet 100 which may be wrapped around the cylinder 104 as described here below. Furthermore, the clip 106 may be envisaged as a hollow cylinder from which a portion D3 of its cylindrical wall has been removed. The size of the opening D3 in the cylindrical wall from which the portion has been removed is preferably smaller than the diameter D2 of the cylinder 104. However, the clip 106 is configured to permit the cylinder to be squeezed into the opening D3, such that the clip bends slightly under elastic deformation to permit entry of the cylinder, and then to snap back so as to hold the cylinder 104 (surrounded by leaflet 100) inside the clip 106. Thus, D1 is sufficiently small to prevent the cylinder 104 from falling out of the bore, once the first cylinder has been received into the bore of the second cylinder.

Following a transcatheter method of delivery that will be described below, the cylinder 104 is positioned above the leaflet 100, and the clip 106 is positioned below the leaflet. The cylinder 104 and clip 106 are then, from this starting position, gently forced towards each other while the leaflet 100 is positioned between them. The cylinder is gently forced through the opening D3 of the clip 106. At a certain point, the clip surrounds the cylinder, and snaps closed to capture the leaflet in a space between the two elements as schematically shown in FIG. 2.

It will be appreciated that, as a consequence of this action, the length of the free edge 102 of the leaflet is effectively shortened because the leaflet becomes wrapped around the cylinder, and is held in position. This shortening of the free edge by transcatheter means is a novel and advantageous result, because it allows the valve to operate with greater coaptation with an opposing leaflet, and thus with renewed efficiency yet eliminates invasive opening of the heart using conventional open heart techniques.

Turning now to FIGS. 3-6, a system and method is described for delivering and attaching the cylinder 104 and the clip on the leaflet as shown in FIGS. 1-2. A delivery catheter 200 is provided. According to known means, it is inserted via transcatheter procedure so that its distal end is positioned within the left atrium of a patient's heart just above the mitral valve. The catheter comprises a number of elements designed to deliver the cylinder 104 and clip 106 combination described above.

Figure 3:
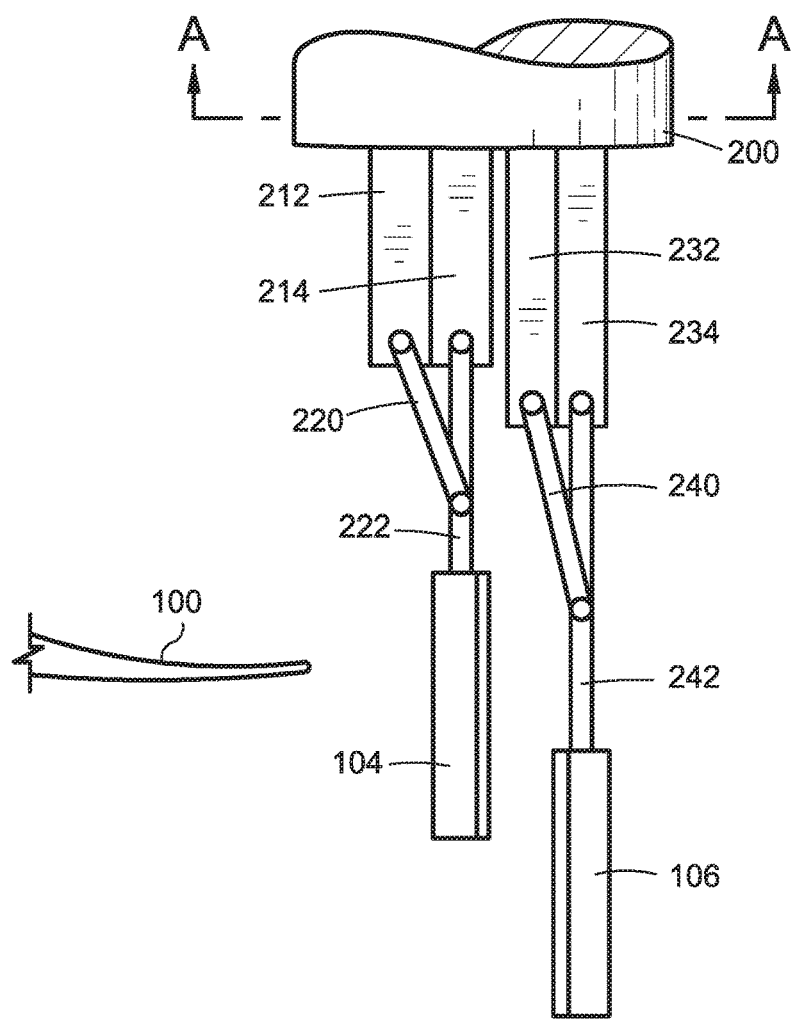
FIG. 3 is a side view of a system for delivering the embodiment in FIG. 1, and shown in a first condition.

With reference to FIG. 3, a first set of delivery elements is provided, namely a first pull element 212 and a first push element 214. These elements are slidingly located within a bore 216 of the catheter (FIG. 4), and may be shaped with a dovetail feature 218 to be slidingly connected to each other, in order to facilitate control. The first set of delivery elements is fitted with two pin-jointed rods, namely a first control rod 220 and a first swivel rod 222. The first control rod 220 is pin-jointed at one end to the first pull element 212 and at the other end to the first swivel rod 222. The first swivel rod 222 is pin jointed at one end to the first push rod 214, and at the other end to the first control rod 220. (Pin joints are depicted as small circles at the ends of the rods.) However, the first swivel rod continues to provide an extended portion that is designed to receive and hold the cylinder 104, as shown in FIG. 3. To enable the first swivel rod to hold the cylinder 104, the cylinder may be provided with an internal bore 105, not necessarily continuous through the cylinder. The first swivel rod may be coated with an expandable malleable substance such as a malleable polymer, so that insertion of the tip of the first swivel rod 222 into the bore 105 of the cylinder 104 will cause the rod to remain within the bore and hold it in position during delivery. Once fully delivered, the swivel rod may be easily removed because the cylinder will be held in a fixed position on the leaflet 100.

A second set of delivery elements is provided, similar to the first set, namely a second pull element 232 and a second push element 234. These elements are slidingly located within a bore 236 of the catheter (FIG. 4), and may be shaped with a dovetail feature 238 to be slidingly connected to each other, to facilitate control using known means. The second set of delivery rods is fitted with two pin-jointed rods, namely a second control rod 240 and a second swivel rod 242, The second control rod 240 is pin-jointed at one end to the second pull element 232 and at the other end to the second swivel rod 242. The second swivel rod 242 is pin jointed at one end to the second push rod 234, and at the other end to the second control rod 240. However, the second swivel rod continues to provide an extended portion that is designed to receive and hold the clip 106, as shown in FIG. 3. To enable the second swivel rod to hold the clip, the clip is already provided with an internal bore. The second swivel rod may be coated with a malleable substance such as a malleable polymer, so that insertion of the tip of the second swivel rod into the bore of the clip will cause the rod to remain within the bore and hold it in position during delivery. Alternatively, the distal end of the second swivel rod may be shaped with its own clasping element to hold the clip 106 on the outside. Once fully delivered, the swivel element may be easily removed because the clip will be held in a fixed position on the leaf 100.

Turning now to a description of the method of deployment of the invention: The catheter is advanced through the mitral valve until the cylinder 104 and the clip 106 at the distal end of the catheter are positioned adjacent the leaflet 100 that is to be operated upon, as shown in FIG. 3.

Figure 5:
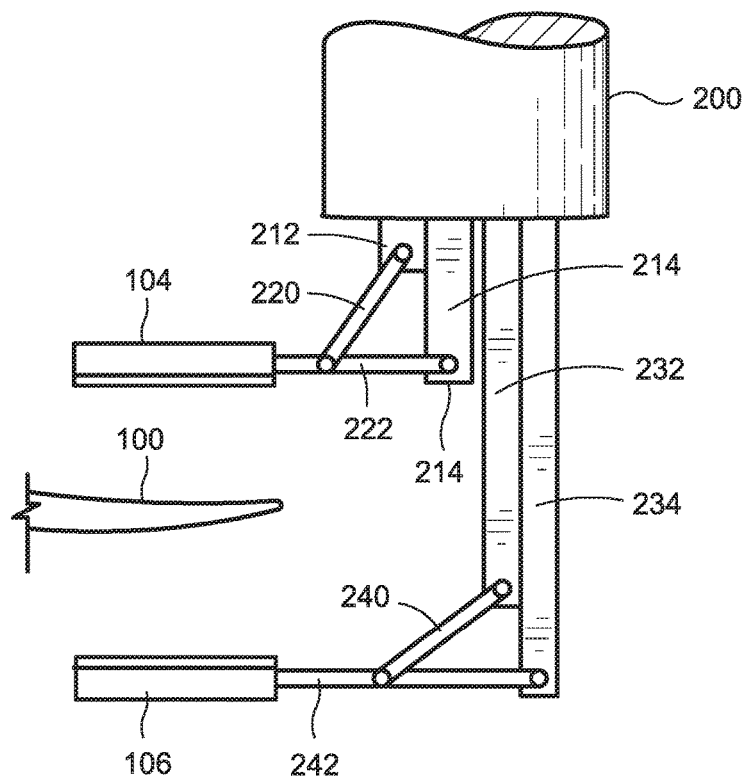
FIG. 5 is a side view of the system for delivering in FIG. 3, and shown in a second condition.

At this point, the first pull element 212 is pulled proximally in relation to the first push element 214; and, the second pull element 232 is pulled proximally in relation to the second push element 234. These movements have the effect of rotating the cylinder 104 and the clip 106 so that they extend perpendicular to the longitudinal axis of the catheter 200, as shown in FIG. 5. At the same time, the longitudinal positions of the cylinder and the clip may be adjusted in relation to each other, by movement of the first set of delivery elements 212, 214 in relation to the second set of delivery elements 232 234. Thus, the physician may both rotate the orientation of the cylinder and clip combination and also adjust their longitudinal separation, by moving the two sets of delivery elements according to known means at the proximal end of the catheter. Finally, the entire system may be rotated about the axis of the catheter. A steering system known in the art may be combined to the system to provide for positioning the system at a precisely desired location.

Figure 6:
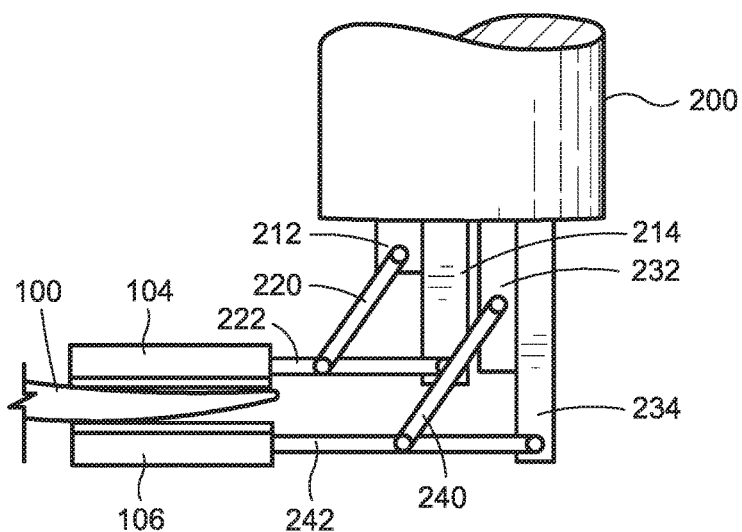
FIG. 6 is a side view of the system for delivering in FIG. 3, and shown in a third condition.

Using this ability to manipulate the cylinder 104 and clip 106, the physician may position the cylinder above the leaflet 100, and the clip below the leaflet, as shown in FIG. 5. Then using further manipulation, the physician moves the cylinder and clip towards each other, to grasp the leaflet, as seen in FIG. 6. Then with a deft movement the physician forces the cylinder and the clip together so that the cylinder passes through the opening D3 in the clip, along with a length of the leaflet 100 that is captured immovably between the cylinder and the clip, as seen in FIG. 2. In this way, the length of the free edge 102 of the leaflet 100 becomes shortened.

In some embodiments, the cylinder and the clip may be fabricated from material of extremely low density, so that the natural frequency of oscillation of the leaf is not substantially altered. In this regard, the cylinder and clip may each be fabricated from a high strength lightweight polymer. In some further embodiments, the polymer may be fiber reinforced. For example the clip will benefit from fiber reinforcement to withstand the bending load applied when the cylinder is forced into the opening D3. In another embodiment, the clip may be formed from an inert shape memory alloy such as Nitinol. And in a further embodiment, the cylinder and clip may be formed to be made of a soft material such as Pebax, so that it does not alter the natural motion of bending of the leaflet to a great extent. Additionally, they may be covered with a porous polyester to promote tissue growth.

Thus, by shortening the free edge of at least one of the mitral valve leaflets, coaptation of a degenerative leaflet may be enhanced. In further embodiments, the free edge of an opposing leaflet may additionally be shortened in exactly the same manner if it is determined that the opposing leaflet would benefit from being shortened.

Figure 7:
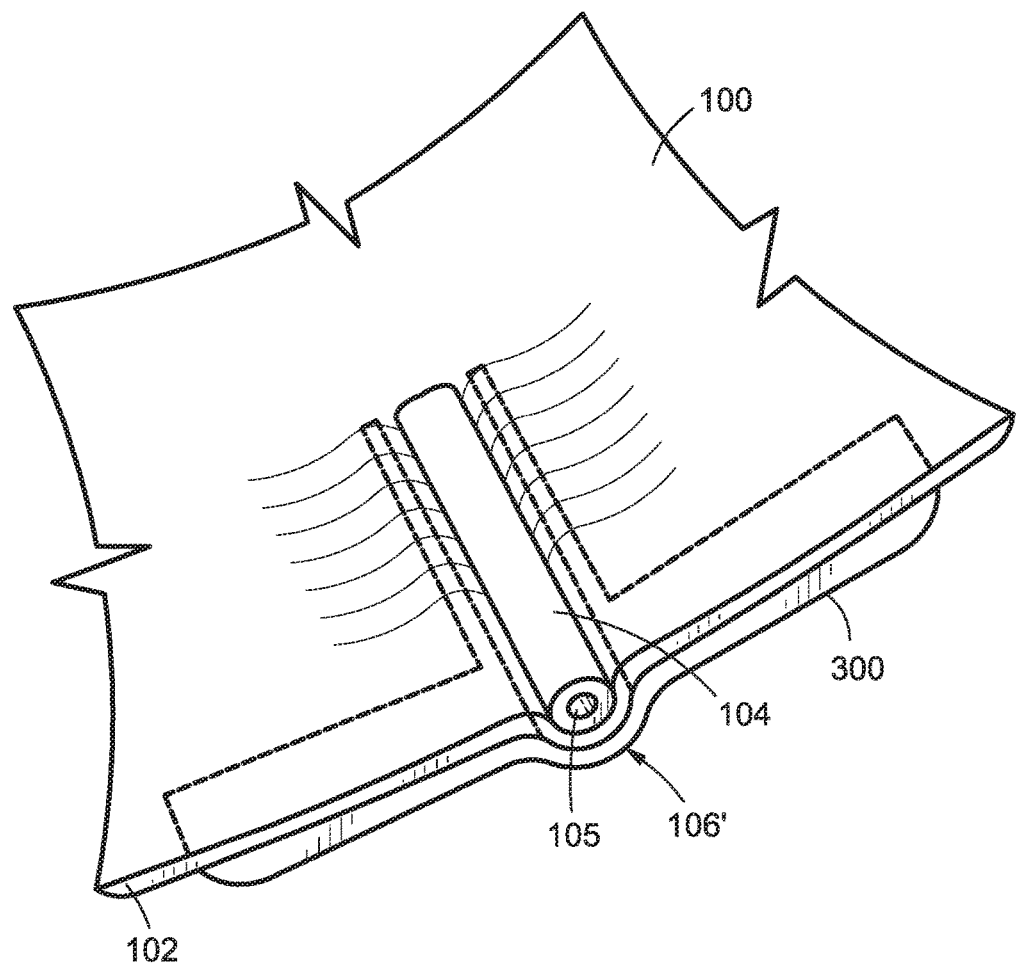
FIG. 7 is a perspective schematic view of another embodiment of the invention, shown attached to a leaflet of a mitral valve.
Figure 8:
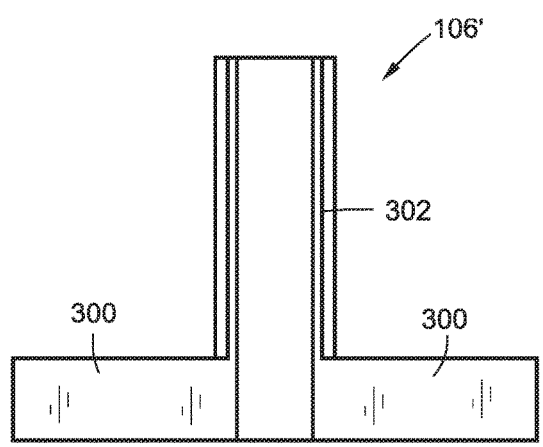
FIG. 8 is a front elevational view of a component of the embodiment in FIG. 7 shown in a first expanded condition.
Figure 9:
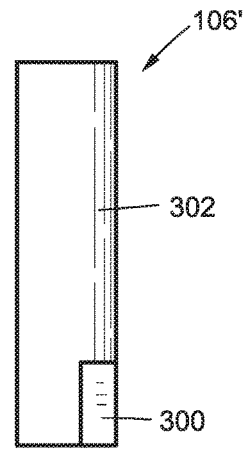
FIG. 9 is a side elevational view of the component in FIG. 7.
Figure 10:
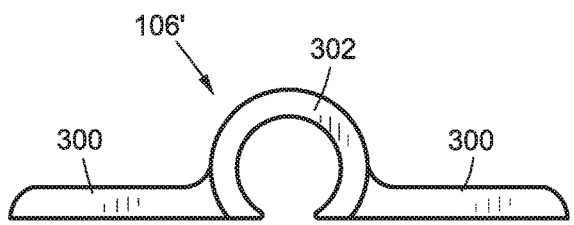
FIG. 10 is a top view of the component in FIG. 7.
Figure 11:
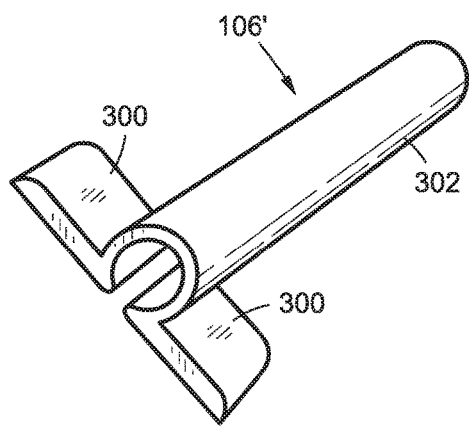
FIG. 11 is a perspective view of the component in FIG. 7.
Figure 12:
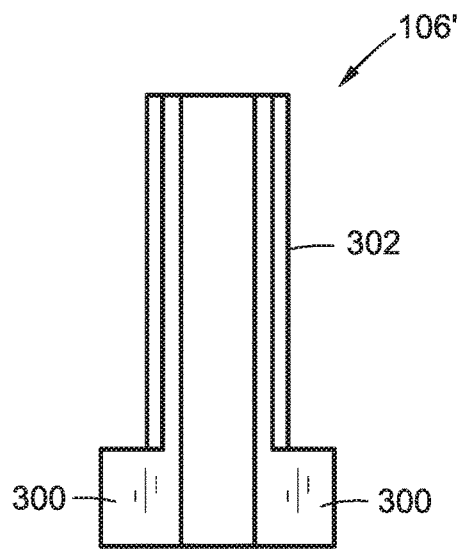
FIG. 12 is a front elevational view of the component of the embodiment in FIG. 7, shown in a second compact condition for delivery.
Figure 13:
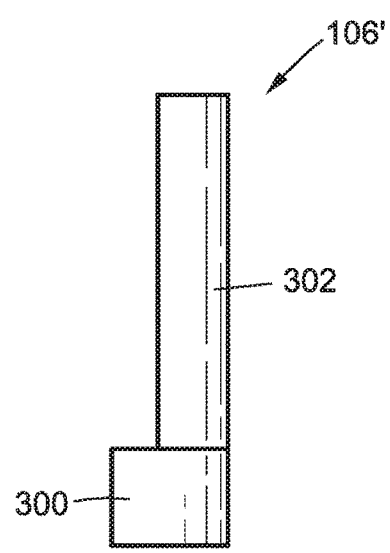
FIG. 13 is a side elevational view of the component in FIG. 12.
Figure 14:
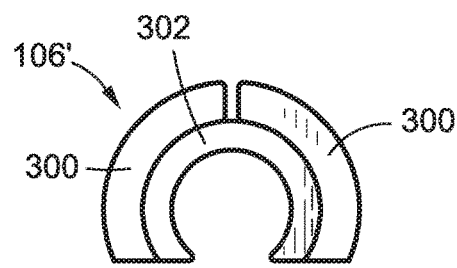
FIG. 14 is a top view of the component in FIG. 12.
Figure 15:
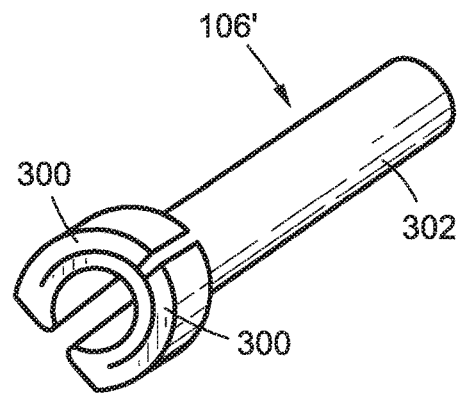
FIG. 15 is a perspective view of the component in FIG. 12.

Turning now to a further embodiment of the foregoing invention, a variation is described with reference to FIGS. 7-15 that provides further advantages under certain conditions. With initial reference to FIGS. 7-11, here, a clip 106' is provided, and is modified to include a set of two flanges 300. The flanges are attached to the clip 106' so that they extend perpendicular to a cylindrical portion 302 of the clip. Two flat surfaces on opposite sides of each flange bound the flange. Thus, when the clip 106' of this embodiment is attached to the cylinder 104 to capture a valve leaflet according to the method described above (with modifications that are set forth here) and as seen in FIG. 7, the flanges 300 extend along the surface of the free edge 102 of the leaflet 100 and support it against bending. This has the advantage that when the leaflet is moved toward an opposing leaflet by blood flow, the leaflet does not tend to buckle at the location of the cylinder, and coaptation with the opposing leaflet is strongly enhanced.

In order to deliver the modified clip 106' to the target location in the heart of a patient, the flanges 300 may be wrapped around the cylindrical portion 302 as exemplified in FIGS. 12-15 in a first compact condition. To enable this aspect, the flanges 300 may be formed from Nitinol, or other shape memory metal so that they assume a desired second expanded shape upon deployment when raised to the body temperature of the patient. However, in the wrapped condition, the clip 106' may be inserted into a confinement portion of the catheter 200 such as a sheath, where it remains in the wrapped condition until it is pushed out of the distal end of the catheter, at which time it assumes the unwrapped condition as shown in FIGS. 7-11. Attachment of the clip 106' to the cylinder 104 as seen in FIG. 7 may be achieved using the same delivery system and method disclosed in FIGS. 3-6. Where deemed necessary, a second modified clip may be attached to an opposing leaflet, so that both leaflets of the mitral valve may achieve enhanced coaptation with each other.

In another aspect, the invention is a method for improving the coaptation of two opposing leaflets of the mitral valve which has suffered from mitral valve prolapse. The method relies upon the same principle as in the embodiments described above, namely, to shorten the length of the free edge of one of the leaflets of the mitral valve, most preferably, the posterior leaflet. While the present embodiment may rely on the use of any kind of clipping system having the features described below, a known structure in the form of the MitraClip™ made by the owner of the present application is a suitable mechanical structure for carrying out the method of the invention. The MitraClip™ is described in principle by U.S. Pat. No. 8,952,592 which is incorporated herein in its entirety.

Figure 16:
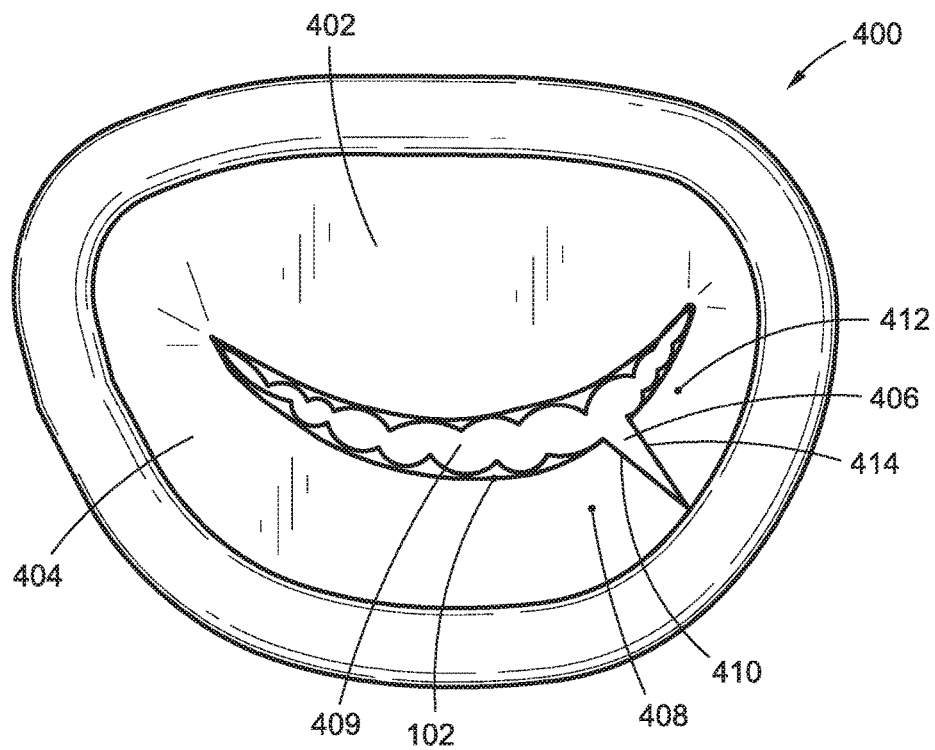
FIG. 16 is a top view of a mitral valve showing anterior leaflet, posterior leaflet, and opening there between, with an incision in the posterior leaflet.

With reference to FIG. 16 there is shown in top view a mitral valve 400 having an anterior leaflet 402 and a posterior leaflet 404. Where prolapse prevents the two leaflets from forming a seal during systole it is desirable to shorten the length of the free edge 102 of the posterior leaflet, because, as may be seen, this leaflet lies on the outside of a bend in the valve aperture 409 formed by the leaflets 402, 404. Shortening the free edge 102 of the posterior leaflet 404 forces the posterior leaflet into closer coaptation with the anterior leaflet 402 during systole and tends to reduce the level of regurgitation.

Figure 17:
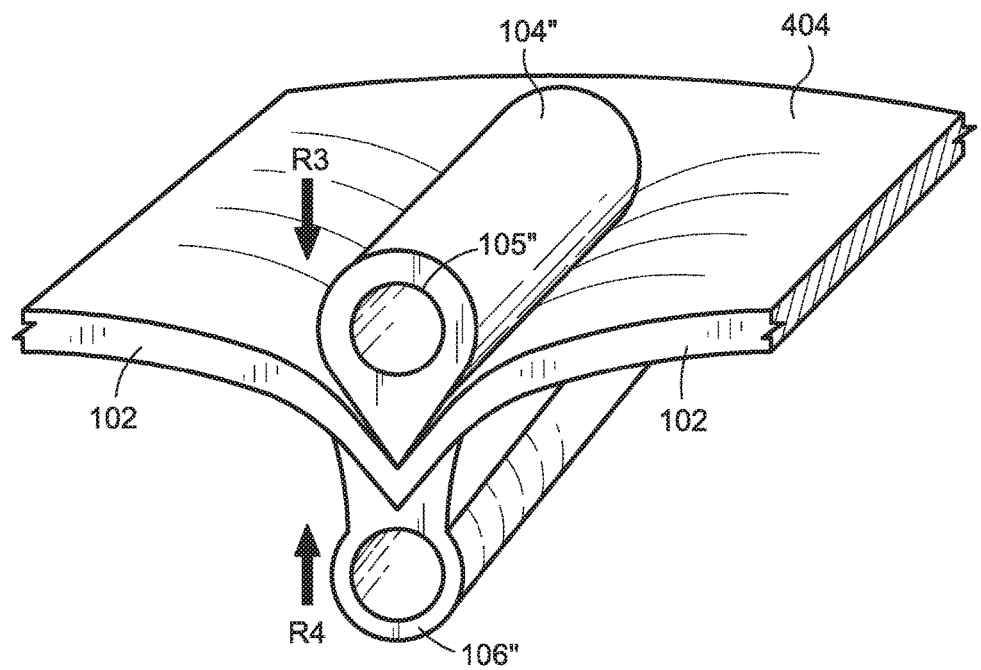
FIG. 17 is a perspective view of yet a further embodiment of the invention, shown in relation to a leaflet of a mitral valve, during the process of cutting the leaflet.

In order to shorten the free edge of the posterior leaflet 404, a first step in this method is, by using transcatheter insertion, to apply a linear cut opening 406 through a leaflet of the mitral valve that is showing signs of prolapse, perpendicular to the free edge 102 of the leaflet. In order to make this cut, the transcatheter device described above with reference to FIGS. 3-6 may be used. However, instead of the cylinder and clip as previously used, two opposing cutting surfaces are inserted onto the swivel rods 222 and 242, as may be envisaged with reference to FIG. 17. In place of the cylinder, a blade element 104" is installed on the first swivel rod 222. In place of the clip, a block element 106" is installed on the second swivel rod 242. The leaflet 404 is captured between the blade element 104" and the block element 106" in the same manner as the leaflet was captured between the cylinder 104 and the clip 106 as described above. This is shown in FIG. 17. The blade element 104" and the block element 106" are then forcibly brought together by relative movement (as indicated by arrows R3, R4) of the first set of delivery elements 212, 214 and second sets of delivery elements 232, 234, so that the blade cuts through the leaflet, leaving the through cut opening 406 as shown in FIG. 16. On the left is a left portion 408 of the leaflet 404, bounded by a left cut edge 410. On the right is a right portion 412 of the leaflet, bounded by a right cut edge 414. (In a further embodiment, the blade and block may be formed so that, instead of having a sharp edge, they are fitted with radio-frequency electrodes configured to cut through the leaflet using electric energy. An example of the technology to be used for this purpose may be found in the Baylis NRG® RF Transseptal Needle.)

Figure 18:
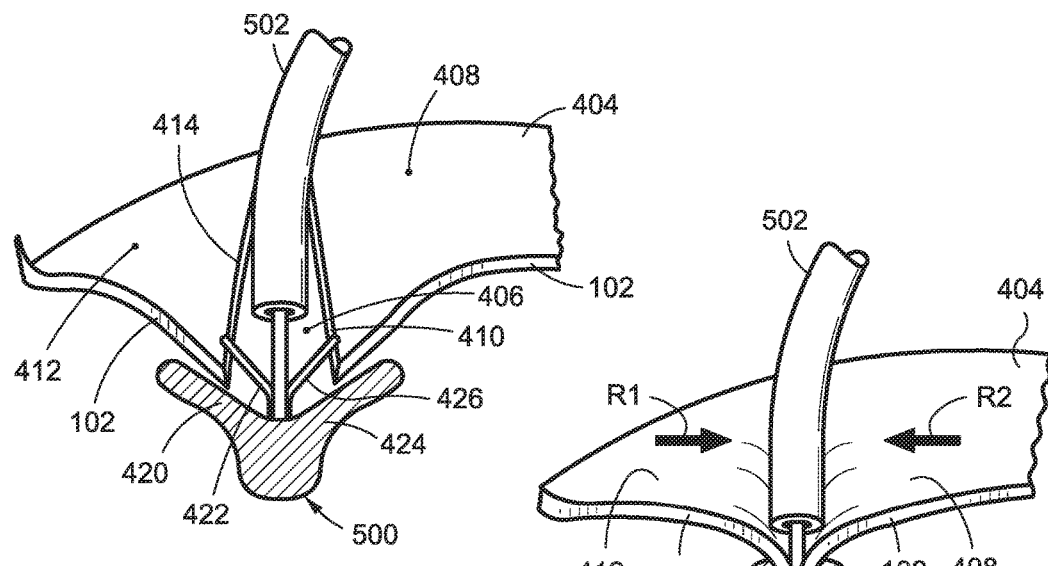
FIG. 18 is a schematic perspective view of a method following a further embodiment of the invention at a first stage of the method.
Figure 19:
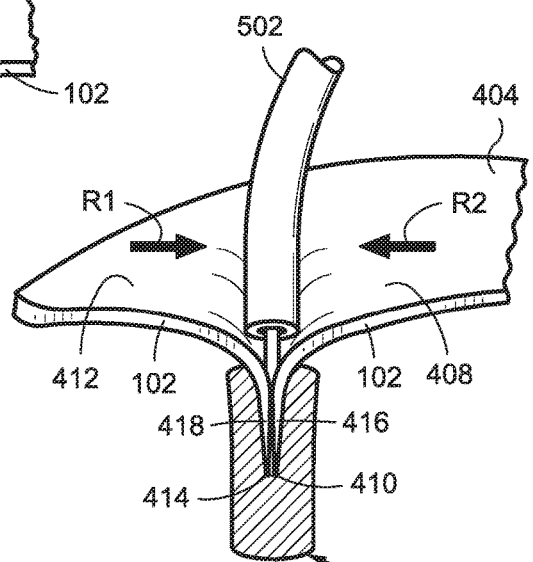
FIG. 19 is a schematic perspective view of the method in FIG. 18 at a second stage of the method.
Figure 20:
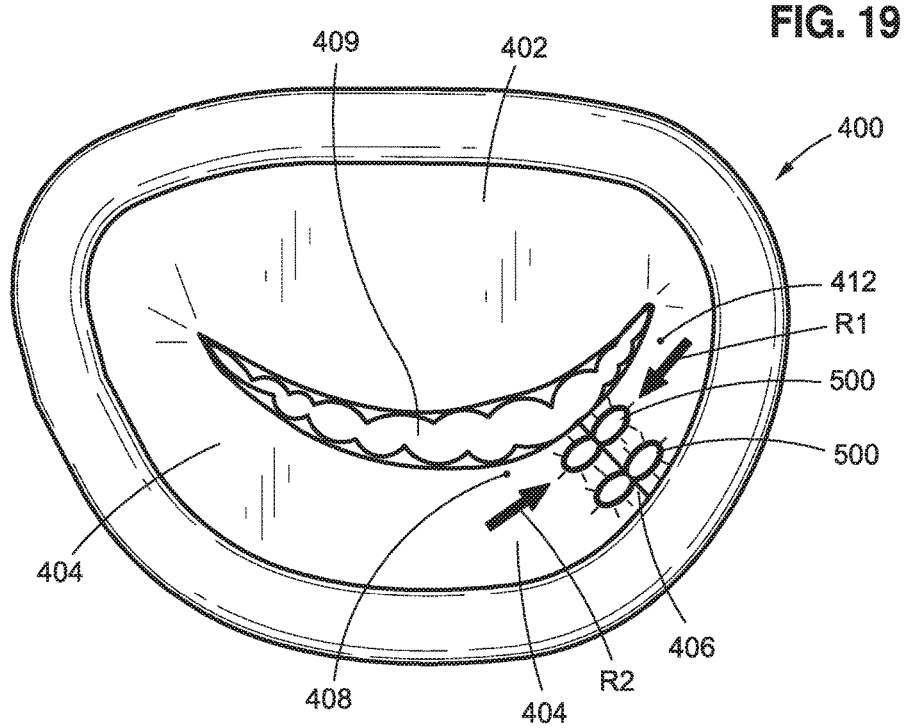
FIG. 20 is a top view of a mitral valve showing anterior leaflet, posterior leaflet, and opening there between, with an incision in the posterior leaflet that has been closed using a method following an embodiment of the invention.

Once the cut opening 406 has been incised into the leaflet 404, a clipping device 500 (such as a MitraCip™) is inserted into the left ventricle of the patient's heart via a delivery element 502 according to known methodology, and is passed through the cut opening 406 in the leaflet, as exemplified in FIG. 18. A feature of the structure of the clipping device, is that it has two sets of opposing jaws namely a first set 420, 422 and a second set 424, 426. Each set is configured to clamp together by known means to capture a portion of a leaflet and hold it. Each set is also configured to fold vertically upwards, so that all jaws are substantially parallel with each other in a vertical direction. (As used herein, the term vertical and horizontal are used to mean an orientation in relation to a heart valve of a patient who is standing vertically.) Due to the structure of the clipping device described here (and also of the MitraClip™) the cut edges 410, 414 of the leaflet are pulled downwards so that terminal portions 416 and 418 (FIG. 19) of the left portion 408 and the right portion 412 respectively, are in contact with each other over a short length and are substantially parallel with each other and extending in a vertical direction, as shown in FIG. 19. The resulting effect is that the left portion 408 and the right portion 412 are pulled toward each other (arrows R1, R2). (As used herein, the term "substantially parallel" shall mean sufficiently parallel as to draw the left portion 408 and the right portion 412 towards each other.) This has the further effect of shortening the effective length of the free edge of the leaflet 404, which is a desired and advantageous effect in that it improves the degree of coaptation between the anterior and posterior leaflets. If the circumstances warrant, a second clipping device 500 may be inserted along the cut edges of the leaflet, which may be understood with reference to FIG. 20.

Accordingly, there are described novel systems that address needs in the art for improving the coaptation between opposing leaves in a mitral heart valve. The present invention may, of course, be carried out in other specific ways than those herein set forth without departing from the essential characteristics of the invention. The present embodiments are, therefore, to be considered in all respects as illustrative and not restrictive, while the scope of the invention is set forth in the claims that follow.

I claim:

1. A system for repairing a mitral valve in a patient's heart, comprising:
   a first cylinder; and
   a clip having an axial length and comprising a second cylinder having a wall and an internal bore, wherein the wall defines an opening extending along the axial length, the opening being sized for at least two requirements:
   (a) the opening is large enough to receive the first cylinder when the first cylinder is positioned parallel with and adjacent to the second cylinder and the first cylinder is moved in a direction, radially with respect to the second cylinder, through the opening into the bore at the same time that a portion of a leaflet in the mitral valve is positioned in the bore between the first cylinder and the second cylinder, wherein, the wall of the second cylinder is sized to bend elastically to widen the opening so as to receive the first cylinder; and (b) the opening is small enough to prevent the first cylinder from falling out of the bore, once the first cylinder has been received into the bore of the second cylinder;

wherein the clip includes two elongate flanges, each flange extending from the second cylinder; and wherein each of the two flanges is configured to be wrapped around the second cylinder when in a delivery condition, and extending perpendicular to the axial length in a deployment condition.

2. The system of claim 1, wherein each of the two flanges are formed from a shape memory alloy.

3. The system of claim 1, wherein each of the two flanges define a surface that is planar.

4. The system of claim 1, wherein the clip is made of polymer.

5. The system of claim 1, wherein the clip is made of shape memory alloy.

6. A method of repairing a mitral valve in a patient's heart utilizing a system as defined in claim 1, comprising:

positioning, above a leaflet of the mitral valve, the first cylinder;

positioning, below the leaflet, the clip having an axial length and comprising a second cylinder having a wall and an internal bore, wherein the wall defines an opening extending along the axial length; and pressing the first cylinder radially toward the second cylinder and through the opening into the bore, and simultaneously forcing a portion of the leaflet into the bore between the first cylinder and the second cylinder.

7. The method of claim 6, wherein pressing the first cylinder through the opening into the bore includes elastically bending the second cylinder to temporarily widen the opening.

8. The method of claim 6, wherein positioning a first cylinder and positioning a clip are performed using a transeptal procedure.

9. The method of claim 6, further including positioning the two elongate flanges to extend along a free edge of the leaflet.

* * * * *